(12) United States Patent
Stanton

(10) Patent No.: US 8,790,331 B2
(45) Date of Patent: Jul. 29, 2014

(54) APPARATUS FOR SEALING ELECTRONICS FROM ENVIRONMENT IN DC POWERED ARTHROSCOPIC SURGICAL HANDPIECE WITH PUSHBUTTON ACTUATION

(75) Inventor: Kevin J. Stanton, Naples, FL (US)

(73) Assignee: Arthrex, Inc., Naples, FL (US)

( * ) Notice: Subject to any disclaimer, the term of this patent is extended or adjusted under 35 U.S.C. 154(b) by 244 days.

(21) Appl. No.: 12/941,570

(22) Filed: Nov. 8, 2010

(65) Prior Publication Data

US 2011/0112518 A1 May 12, 2011

Related U.S. Application Data

(60) Provisional application No. 61/259,979, filed on Nov. 10, 2009.

(51) Int. Cl.
| | |
|---|---|
| A61B 19/00 | (2006.01) |
| H01H 13/14 | (2006.01) |
| H01H 25/00 | (2006.01) |
| H01H 13/76 | (2006.01) |
| H01H 23/06 | (2006.01) |
| H01H 13/06 | (2006.01) |
| A61B 17/00 | (2006.01) |

(52) U.S. Cl.
CPC ...... *H01H 23/06* (2013.01); *A61B 2017/00367* (2013.01); *H01H 13/06* (2013.01)
USPC ............... 606/1; 200/341; 200/337; 200/5 A

(58) Field of Classification Search
CPC ............ H01H 2223/014; H01H 13/06; H01H 2223/002; H01H 2300/014; H01H 23/06; A61B 2017/00367
See application file for complete search history.

(56) References Cited

U.S. PATENT DOCUMENTS

| | | | | |
|---|---|---|---|---|
| 4,218,602 | A * | 8/1980 | Creech ....................... | 200/302.3 |
| 4,366,463 | A | 12/1982 | Barker | |
| 6,214,003 | B1 | 4/2001 | Morgan et al. | |
| 6,500,169 | B1 * | 12/2002 | Deng ................................. | 606/1 |
| 2003/0174590 | A1 * | 9/2003 | Arikawa et al. ............... | 368/319 |
| 2005/0109602 | A1 * | 5/2005 | Parkinson et al. ............. | 200/511 |
| 2009/0014297 | A1 * | 1/2009 | Sakaguchi et al. .......... | 200/302.2 |
| 2009/0194400 | A1 * | 8/2009 | Mackay ...................... | 200/302.2 |
| 2011/0048909 | A1 * | 3/2011 | Clark et al. ................... | 200/330 |

OTHER PUBLICATIONS

DSM Engineering Plastics, Technical Guide ("Snap Fit Theory", Feb. 23, 2005).*

* cited by examiner

*Primary Examiner* — Gary Jackson
*Assistant Examiner* — Scott T Luan
(74) *Attorney, Agent, or Firm* — Dickstein Shapiro LLP

(57) ABSTRACT

A button for actuating a switch in a surgical handpiece. The button is sealed to a bezel, and the bezel is sealed to the handpiece. The button, bezel, and handpiece create a sealed enclosure surrounding the switch to prevent external substances from contacting the switch. Further, a control board for controlling the handpiece is embedded in a cable endcap instead of being housed within the handpiece.

22 Claims, 12 Drawing Sheets

APPARATUS FOR SEALING ELECTRONICS FROM ENVIRONMENT IN DC POWERED ARTHROSCOPIC SURGICAL HANDPIECE WITH PUSHBUTTON ACTUATION

This application claims the benefit of Provisional Application No. 61/259,979, filed Nov. 10, 2009.

BACKGROUND OF THE INVENTION

1. Field of the Invention

The present invention relates to systems for sealing electronic devices in surgical handpieces from outside elements during surgical use, post-use cleaning, or sterilization.

2. Description of the Related Art

In conventional switch designs of surgical handpieces, the sealing strength depends on the pressure of the bezel attachment. For example, switch circuitry in conventional systems often employs a conductive pill or snap-dome actuation. These switches are sealed within the housing with a large elastomer membrane that is placed over the entire switch cavity and held in place with a bezel. The pressure of the bezel against the housing creates a seal. After being sealed, however, the switch many times does not reliably actuate because the seal fails.

There is a need for new designs for sealing electronics within handpiece so switches may be properly sealed and actuate reliably. Also, there exists a need for a handpiece design that it easier to assemble and is impervious to any factor that may affect its normal use.

Additionally, unlike conventional designs of surgical handpieces in which the microprocessor and other circuitry is typically located within the housing, it would be desirable to locate the microprocessor and associated circuitry closer to the handpiece but also seal and protect the circuitry from water, contaminants, or sterilization liquids.

SUMMARY OF THE INVENTION

Embodiments of the present invention provide for sealing electronic devices of a surgical handpiece from outside elements during surgical use and/or post-use cleaning and/or sterilization. In one embodiment, the microprocessor circuitry of the handpiece is embedded in the cable and potted, so that no external or internal factors (such as liquid, for example) may impede the function of the circuitry.

Another embodiment provides for a surgical handpiece that includes a sealed switch for controlling the handpiece. The handpiece also has a bezel with a button sealed within an opening in the bezel. The bezel is positioned to align the button over the switch so that the button can actuate the switch. The button, the bezel, and the handpiece form a sealed enclosure around the switch to protect the switch from outside elements during surgical use.

In another embodiment, a linkage transfers a force applied to the button, to the switch, to actuate the switch. Further, the button may be sealed to the bezel using an x-ring or o-ring seal. Additionally, the button may be formed of an elastomeric material and have a bulge that seals the button to the bezel.

In another embodiment, the opening in the bezel extends through the entire bezel and the button comes into contact with the switch. Further, the opening in the bezel may not extend through the entire bezel and an insert may be placed partially within the button to hold the button with the opening of the bezel.

Another embodiment provides for a handpiece that has a second switch. Here, the bezel has a second button within a second opening of the bezel. The second button is sealed to the bezel and a downward force applied to the second button causes the second switch to actuate. The first and second switches are sealed together in an enclosure created by the first and second button, the bezel, and the handpiece.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

Figure 11:
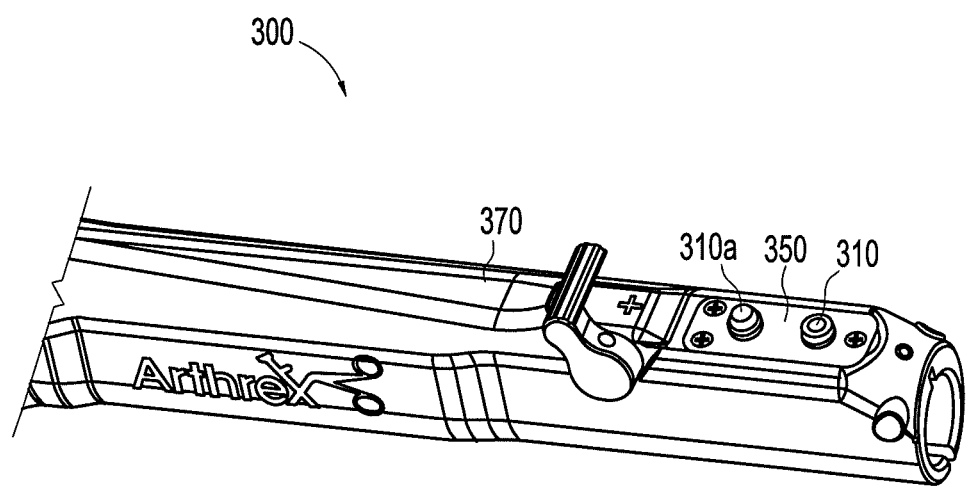
FIG. 11 illustrates two buttons within a bezel attached to a housing according to one embodiment.
Figure 12:
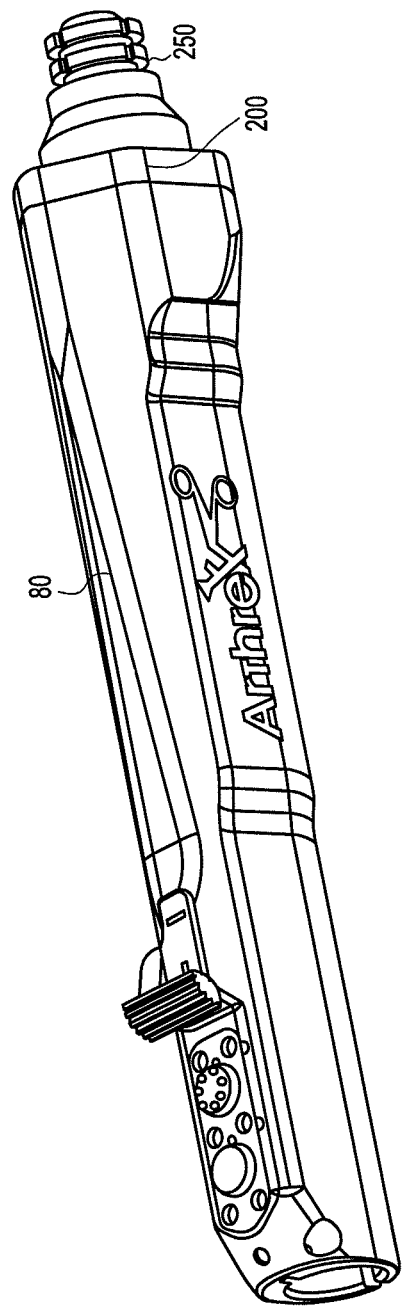
FIG. 12 illustrates a surgical handpiece with an attached cable according to one embodiment.
Figure 13:
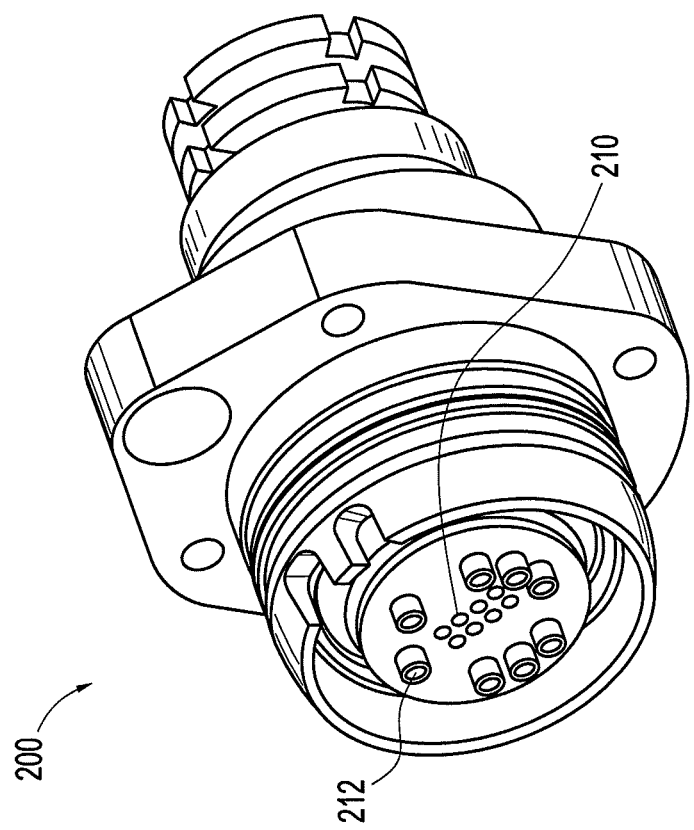
FIG. 13 illustrates a cable end piece according to one embodiment.
Figure 14:
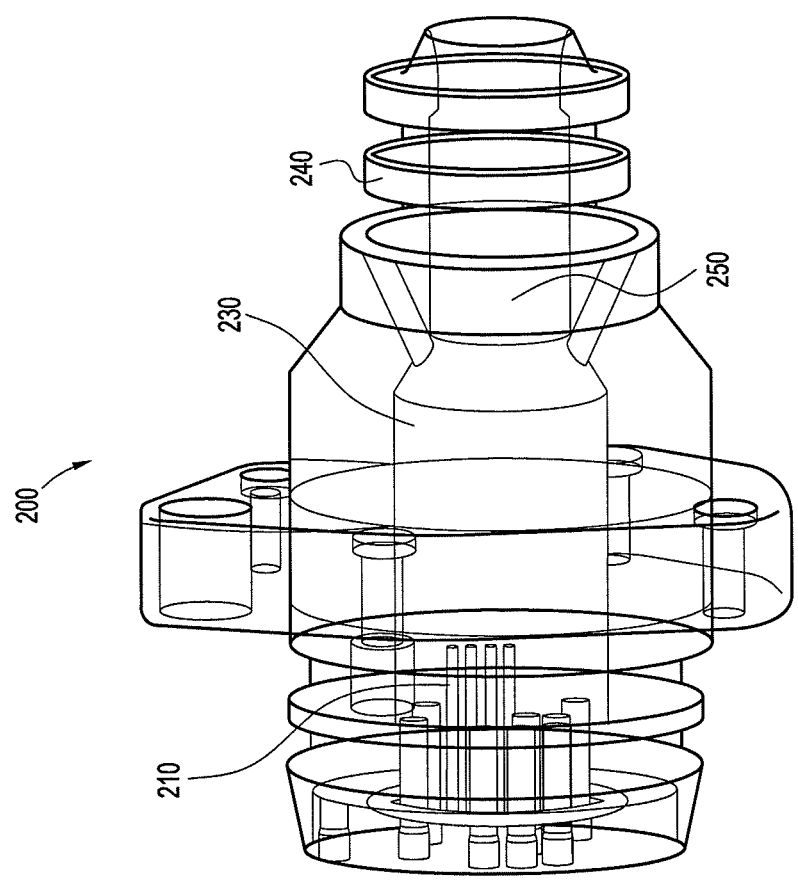
FIG. 14 illustrates a perspective view of a cable end piece according to one embodiment.

Referring now to the drawings, where like elements are designated by like reference numerals, FIGS. 1-6 illustrate various views of an exemplary pushbutton configured to seal a switch and PCB board inside a handpiece to prevent foreign objects, such as, water, contaminants or sterilization liquid, from reaching the switch and PCB board. FIGS. 7-11 illustrate various views of a second exemplary pushbutton. FIGS. 12-14 illustrate various views of an exemplary assembly 200 wherein the handpiece control circuitry is embedded in the cable and potted.

Figure 1:
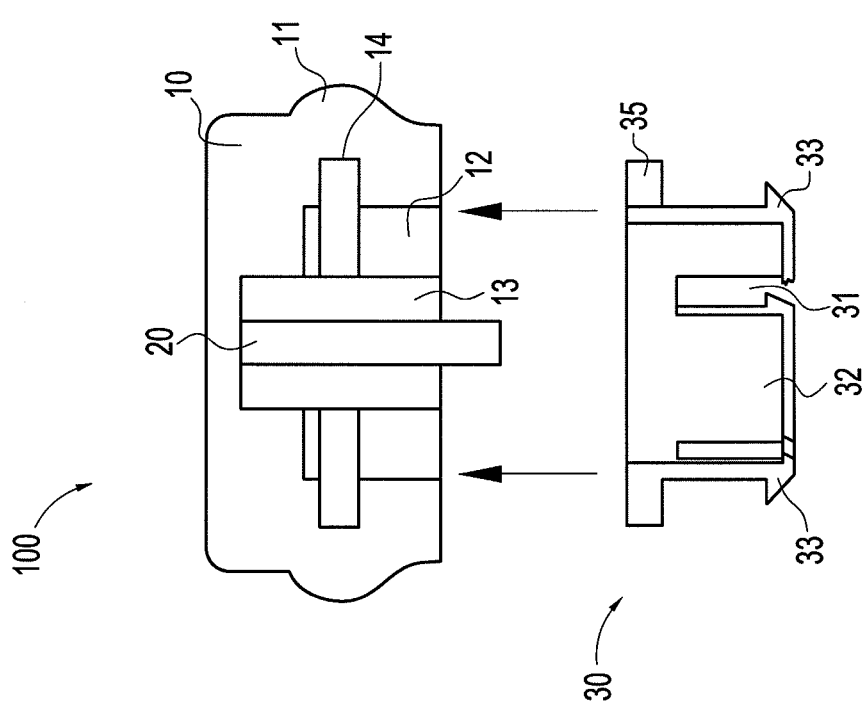
FIG. 1 illustrates a cross-sectional view of a button and insert according to one embodiment.

FIG. 1 illustrates button 10, linkage 20, and button insert 30 that form part of pushbutton system 100. Button 10 has a cylindrical shape and is formed of an elastomeric material. Button 10 also has bulge 11 between the top and bottom part of button 10 that extends away from the center of button 10. Button 10 further includes insert channel 12 that has a circular shape and a depth that extends from the bottom of button 10 toward the top of button 10 and surrounds button extension 13. Button 10 also includes arm channel 14, which is circular in shape and extends through the middle of button 10. In one embodiment, the middle of arm channel 14 may be approximately aligned with the middle of bulge 11. Arm channel 14 further intersects with insert channel 12 and together they form an inverted L shaped opening within button 10.

Figure 5:
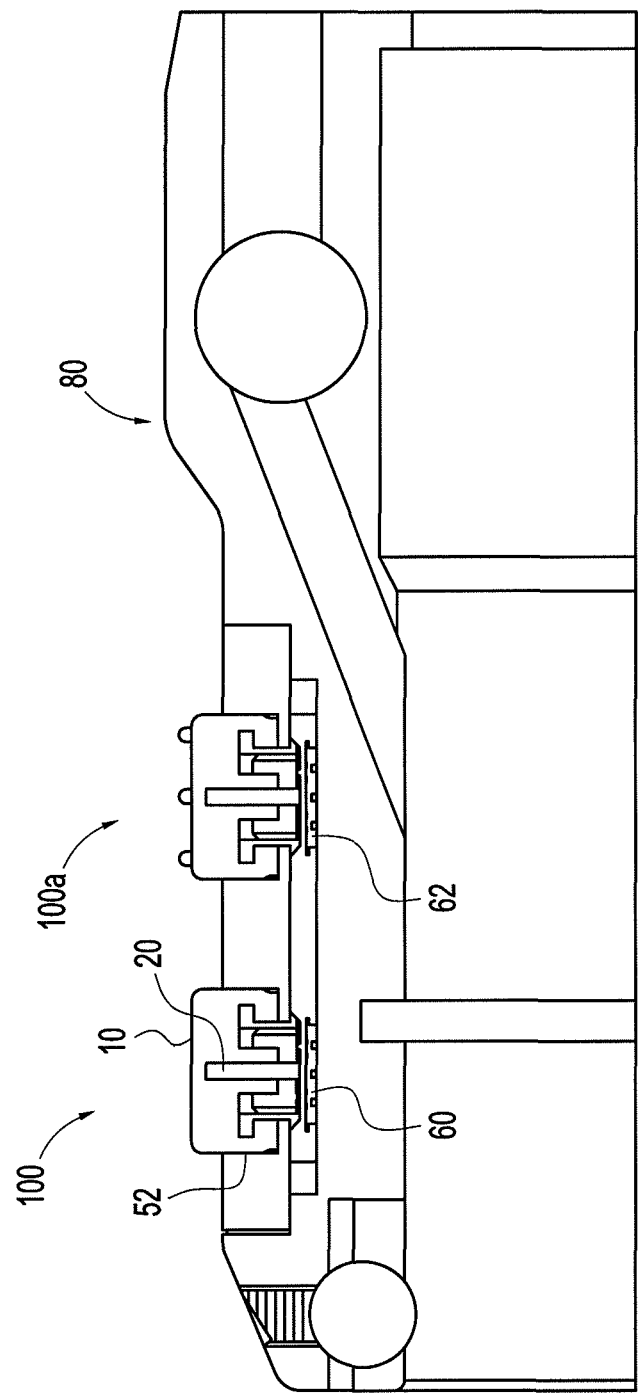
FIG. 5 illustrates two button systems within a bezel attached to a housing according to one embodiment.

Pushbutton system 100 further includes linkage or knob 20. Linkage 20 is a straight member that is partially contained within button 10 and extends through button arm 13 and away from the bottom of button 10. Linkage 20 may also have a T shape as shown in FIG. 5, where the cross portion resides within button 10.

Pushbutton system 100 further includes insert 30. Insert 30 has a hollow cylindrical shape. Insert 30 has, on one end, insert flange 35 that extends away from the center of insert 30 and around the periphery of insert 30. On the other end, insert 30 has slits 31 that extend toward insert flange 35. The portions of insert 30 that are between slits 31 form individual insert tabs 32. Insert tabs 32 individually flex toward and away from the center of insert 30. Each insert tab 32 has tab flange 33 at their open end that extends away from the center of insert 30. In pushbutton system 100, insert 30 is placed within insert channel 12 so that button 10 surrounds a portion of insert 30 and insert flange 35 is placed within arm channel 14. Tab flanges 33 remain outside of button 10.

Figure 2:
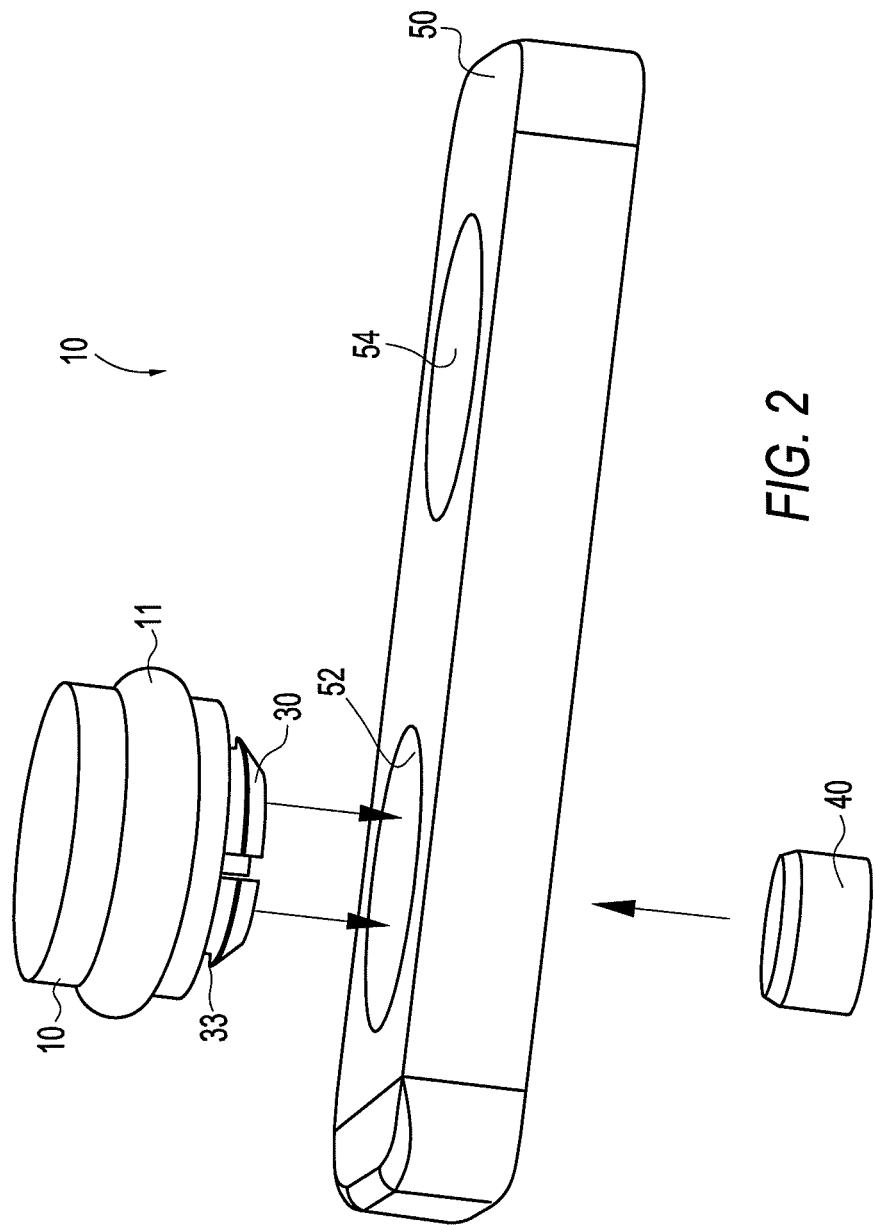
FIG. 2 illustrates a cross-sectional view of a button and bezel according to one embodiment.
Figure 3:
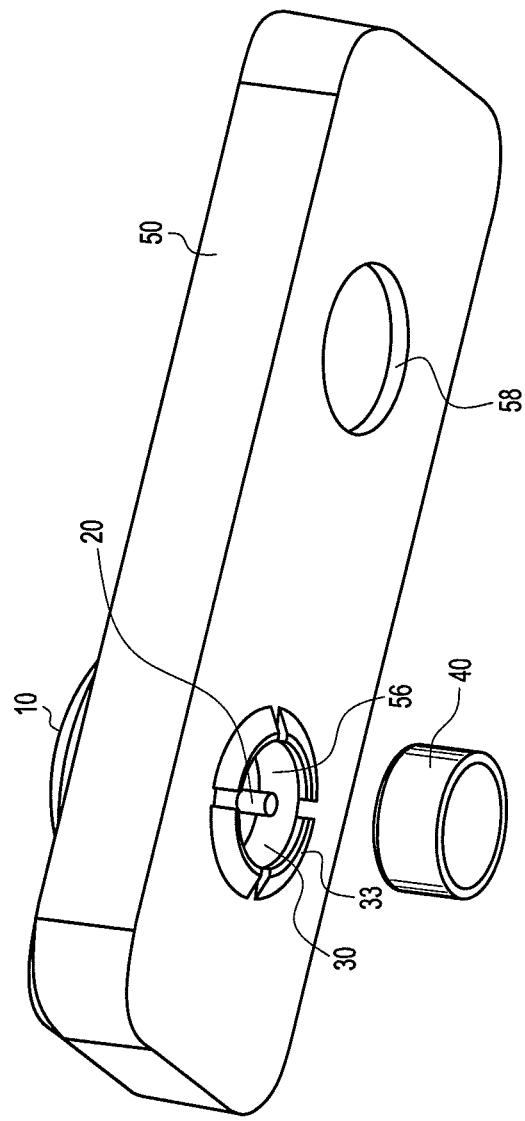
FIG. 3 illustrates another view of the button and bezel of FIG. 2.

FIGS. 2 and 3 illustrate tube 40, which also forms a part of pushbutton system 100. FIGS. 2 and 3 also illustrate bezel 50 that has button openings 52, 54 formed to accept button 10 on a first side. Button 10 is placed within button opening 52 so that the entire bulge 11 of button 10 is within button opening 52.

As shown in FIG. 3, button 10 is not wholly located within button opening 52, but a portion of button 10 extends away from bezel 50. Further, button openings 52, 54 do not extend all the way through bezel 50. On a second side, opposite the first side, bezel 50 has insert openings 56, 58 that extend through bezel 50 to meet buttons openings 52, 54, respectively. Insert openings 56, 58 have a smaller diameter than button openings 52, 54 that do not allow passage of button 10. With button 10 placed within button opening 52, a portion of insert tabs 32 extend away from of bezel 50 and opening 56 and tab flanges 33 extend over the surface of the second side of bezel 50. Tab flanges 33 assist in keeping button 10 within button opening 52. As shown in FIG. 3, linkage 20 extends through insert 30 and through insert opening 56.

Tube 40 is located within insert 30, is in contact with, and applies a force to insert tabs 32, thereby forcing insert tabs 32 toward the outer edges of insert opening 56 and against button 10. The pressure on insert 30 caused by tube 40 maintains button 10 within button opening 52. Further, the pressure on button 10 from insert 30 causes bulge 11 to press against the side of button opening 52 causing a seal to form between button 10 and bezel 50.

It should be understood that button 10, insert 30, tube 40, button openings 52, and insert opening 56 may be any shape that allows button 10 to be secured to and form a seal with bezel 50 in the manner described above. For example, button 10, insert 30, tube 40, button openings 52, and insert opening 56 may have a hexagon shape or some other form or shape.

Figure 4:
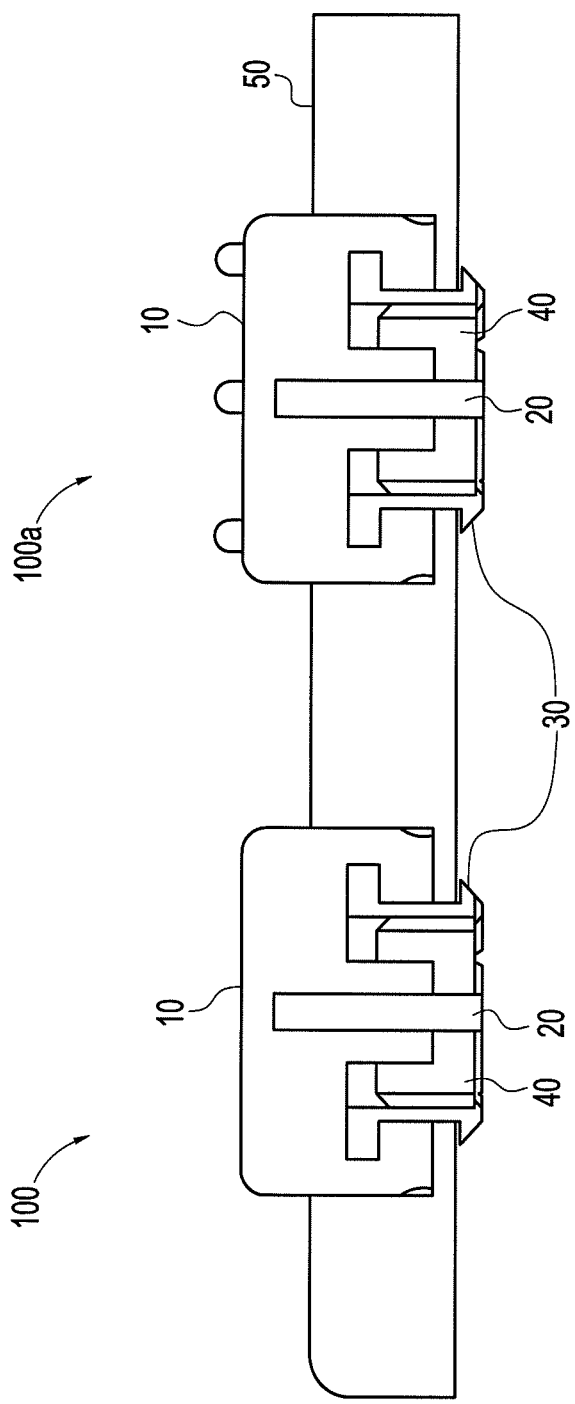
FIG. 4 illustrates two button systems within a bezel according to one embodiment.

FIG. 4 illustrates a cross-sectional view of two pushbutton systems 100, 100a. Both pushbutton systems 100, 100a include button 10, linkage 20, insert 30, tube 40, and are attached to bezel 50. An exemplarily method of assembling the structure shown in FIG. 4 is now describe. During assembly, an insert 30 is pressed into button 10, and then button 10 is snapped into bezel 50. The bezel assembly (bezel 50 with embedded buttons 10) is flipped over and tubes 40 are pressed into embedded button 10. This process is repeated for each button 10 within a bezel.

Figure 6:
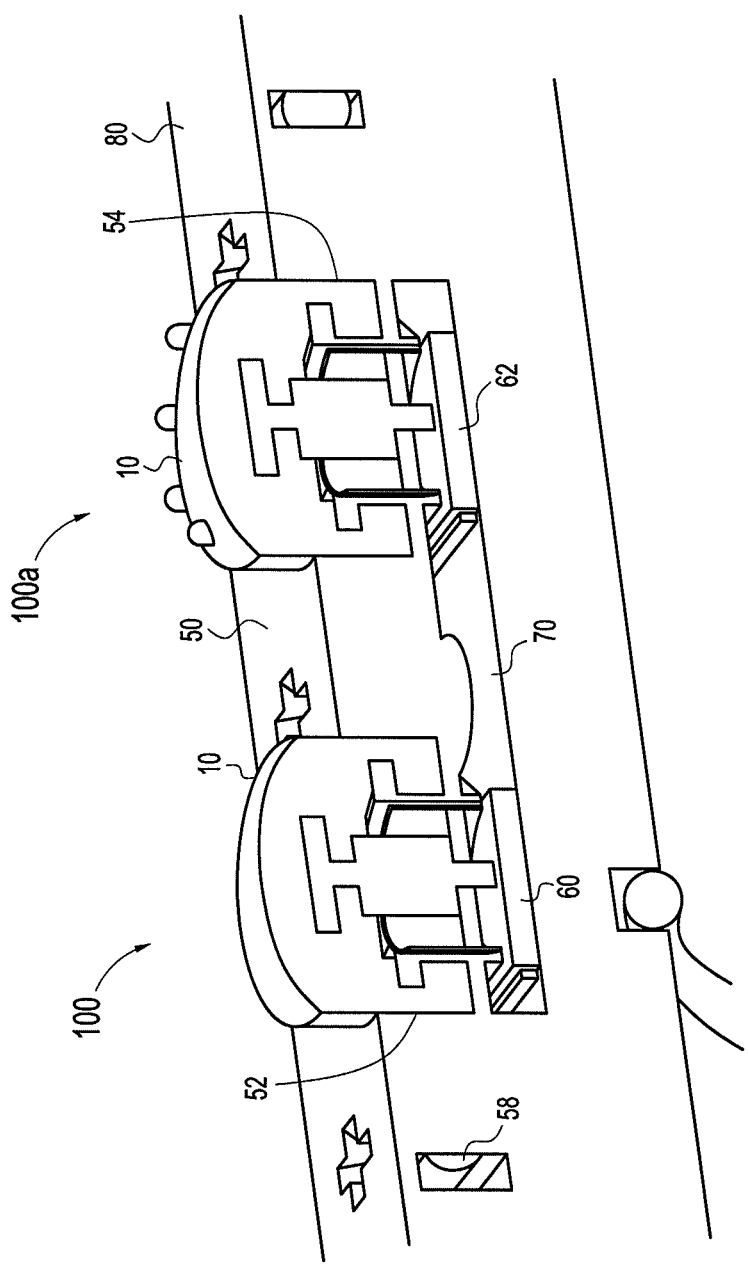
FIG. 6 illustrates another view of the embodiment illustrated in FIG. 5.

FIGS. 5 and 6 illustrate a cross-sectional view of two pushbutton systems 100, 100a attached to bezel 50, with bezel 50 attached to housing 80 of a surgical handpiece. Housing 80 includes switches 60, 62 attached to a rigid PCB 70 (shown in FIG. 6). Switches 60, 62 are used to control the surgical handpiece. Bezel 50 is aligned so that button openings 52, 54 are over switches 60, 62 respectively.

The actuation of switches 60, 62 using button systems 100, 100a, respectively, is now explained. With button opening 52 aligned over switch 60, a downward force is applied to button 10 of button system 100 to actuate switch 60. As the downward force is exerted on button 10, button 10 flexes and forces linkage 20 of button system 100 downward toward switch 60. Linkage 20 then contacts switch 60 and exerts a force on switch 60, causing switch 60 to connect or disconnect a circuit in PCB 70. In essence, linkage 20 transfers force applied to button 10 to switch 60 thereby actuating switch 60. When switch 60 actuates, it connects or disconnects a circuit in PCB 70, thereby controlling the handpiece. In a similar manner button system 100a actuates switch 62. In this embodiment, switches 60, 62 may be a tactile switch, snap-dome switch, conductive pill switch, or some other type of switch.

FIG. 6 also illustrates seal 58 provided between bezel 50 and housing 80. Seal 58 may be an o-ring seal, an x-ring seal, or any other type of device that is able to create a seal between bezel 50 and housing 80. When bezel 50 is sealed to housing 80 and buttons 10 from pushbuttons systems 100, 100a, a sealed enclosure is formed by bezel 50, buttons 10, and housing 80 that encases switches 60, 62 and PCB 70. In this manner, switches 60, 62 and PCB 70 are sealed so that external material such as water, contaminants, sterilization liquid, and others are prevented from contacting switches 60, 62 and PCB 70.

Figure 7:
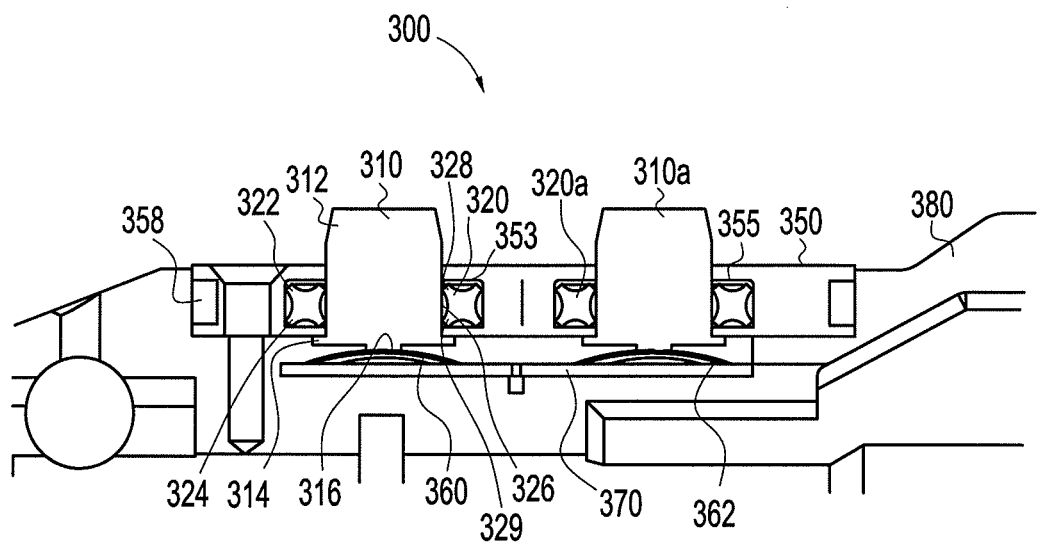
FIG. 7 illustrates two buttons within a bezel attached to a housing according to one embodiment.

FIG. 7 illustrates another embodiment of surgical handpiece 300. Handpiece 300 includes buttons 310, 310a, button seals 320, 320a, bezel 350, bezel seal 358, switches 360, 362, PCB 370, and housing 380. Button 310 has cylinder body 312 with flange 314 at a first end that extends away from the middle of button 310. Button 310 further includes protrusion 316 at the first end. Protrusion 316 extends away from the first end of button 310 and perpendicular to flange 314.

Figure 8:
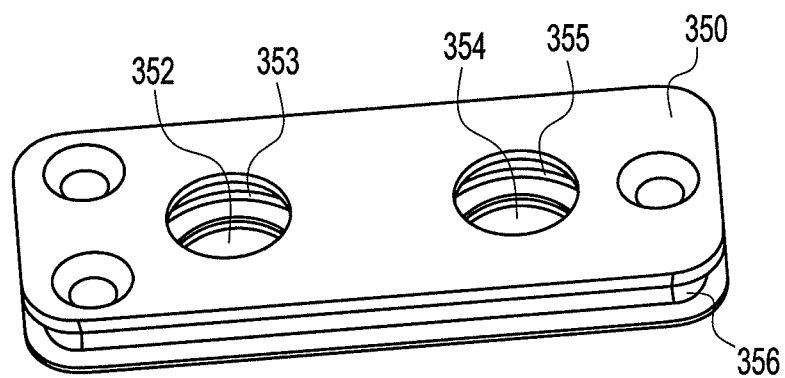
FIG. 8 illustrates a bezel according to one embodiment.

FIG. 8 illustrates bezel 350. Bezel 350 has button openings 352, 354 that extend through bezel 350 and bezel groove 356 for accepting an o-ring. Openings 352, 354 are circular and have a sufficient diameter to allow button body 312 to pass through but not button flange 312. The internal walls of openings 352, 354 also include grooves 353, 355, respectively, that extend into bezel 350 and away from the middle of openings 352, 354. Grooves 353, 355 house button seals 320, 320a. One exemplary button seal 320 is described with respect to FIG. 9.

Figure 9:
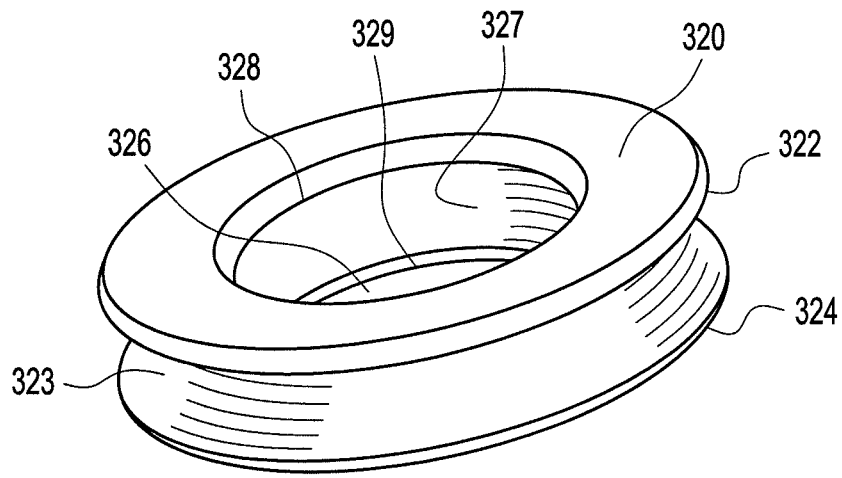
FIG. 9 illustrates a seal according to one embodiment.

FIG. 9 illustrates button seal 320. Button seal 320 is a circular ring with a hollow center 326. Center 326 has a diameter sufficient to allow button body 312 to pass through. Button seal 320 further includes outer channel 323 that passes along the outer periphery of button seal 320 and forms outer sealing ridges 322, 324. Button seal 320 also includes inner channel 327 that passes along the interior periphery of button seal 320 and forms interior sealing ridges 328, 329. Interior sealing ridges 328, 329 and outer sealing ridges 322, 324 together form an X shape. Button seal 320a is similar to button seal 320.

FIG. 7 illustrates groove 353 of bezel 350 housing button seal 320 and groove 355 of bezel 350 housing button seal 320a. FIG. 7 further illustrates button body 312 passing through opening 352 and center 326 of button seal 320 and extending away from bezel 350. With button body 312 and bezel 350 in contact with button seal 320, outer sealing ridges 322, 324 of button seal 320 each form a seal with bezel 350, and inner sealing ridges 328, 329 of button seal 320 each form a seal with button 310. As a result, button 310 is sealed to bezel 350. Button 310a is similarly sealed to bezel 350 by button seal 320a. Bezel 350 is also sealed to housing 380 by bezel seal 358, which is provided between bezel 350 and housing 380. Bezel seal 358 may be an o-ring seal, an x-ring seal, or any other type of device that is able to create a seal between bezel 350 and housing 380. With bezel 350 sealed to housing 380 and buttons 310, 310, a sealed enclosure if formed by bezel 350, buttons 310, 310a, and housing 380 that encases switches 360, 362 and PCB 370. In this manner, switches 360, 362 and PCB 370 are sealed so that external material such as water, contaminants, sterilization liquid, and others are prevented from contacting switches 360, 362 and PCB 370.

FIG. 7 further illustrates button 310 in contact with switch 360. To actuate switch 360, a downward force is applied to button 310. Button 310 shifts downward and button lip 314 moves out of contact with bezel 350. Button protrusion 316 moves downward with button 310 and forces switch 360 downward and into contact with PCB 370. As switch 360 contacts PCB 370, switch 360 connects or disconnects a circuit in PCB 370 thereby controlling handpiece 300. Once pressure is released from button 310, switch 360 has a spring constant that allows it to push away from PCB 370 and force protrusion 316 and button 310 upward until button lip 314 contacts bezel 350.

In another embodiment, button protrusion 316 is not in contact with switch 360 before a force is applied to button 310. Further, button lip 314 may not be in contact with bezel 350 before or after force is applied to button 310.

Figure 10:
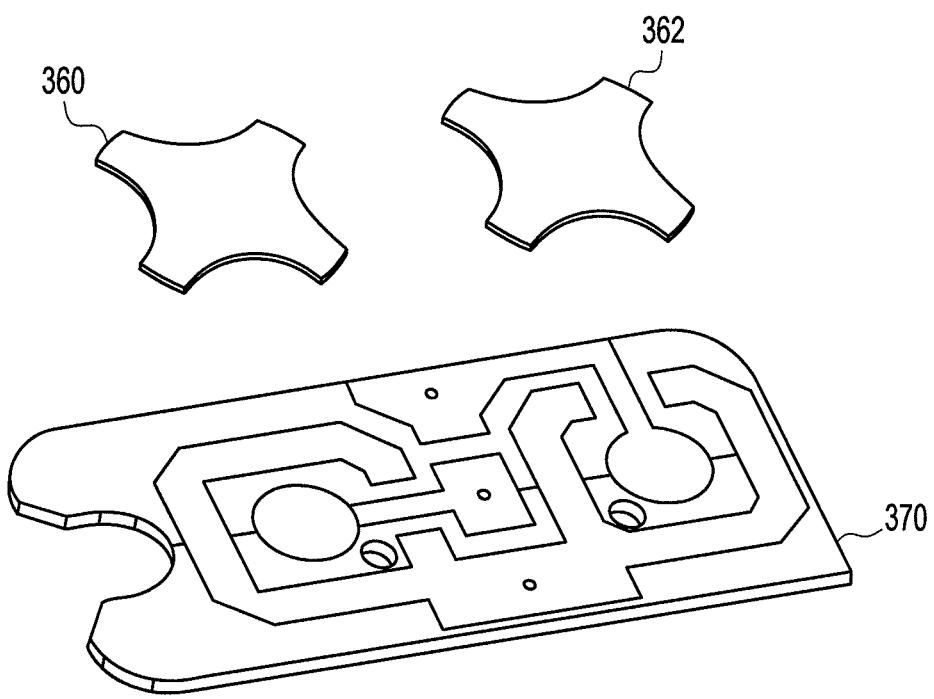
FIG. 10 illustrates a switch and PCB according to one embodiment.

FIG. 10 further illustrates switches 360, 362 and PCB 370. Switches 360, 362 may be dome switches or another type of switch. FIG. 11 illustrates handpiece 300 with buttons 310, 310a attached to bezel 350, which is attached to housing 370.

The above-described embodiments are improvements over the conventional systems known in the art which use a conductive pill or snap-dome actuation with a large elastomer membrane over the entire switch cavity to seal it. The sealing strength of these conventional systems depends upon the pressure of the bezel attachment. The methods of actuation of the conventional systems are also not reliable. The embodiments described above overcome these disadvantages.

Referring now to FIGS. 12-14, in one embodiment housing 80 of a handpiece is connected to cable 250 that has cable endcap 200. In this embodiment, cable endcap 200 includes control circuitry for the handpiece, such as a microprocessor. As shown in FIG. 13, cable endcap 200 includes a plurality of female PCB control connectors 210 and a plurality of female motor control connectors 212. Female connectors 210, 212 receive male connectors from housing 80 thereby electrically coupling together housing 80 and cable endcap 200. Further, as shown in FIG. 14, female PCB control connectors 210 are soldered or otherwise electrically connected to control board 230 that is embedded and potted in endcap 200. Control board 230 is further connected to cable contacts 240 of cable 250. Cable 250 is connected to a console that sends instructions to and receives information and feedback from control board 230. Control board 230 is used to control a motor or some other mechanism within housing 80 of the surgical handpiece.

Although the present invention has been described in relation to particular embodiments thereof, many other variations and modifications and other uses will become apparent to those skilled in the art.

What is claimed as new and desired to be protected by Letters Patent of the United States is:

1. A surgical handpiece comprising:
   a switch connected to the handpiece and used for controlling the handpiece;
   a bezel sealed to the handpiece, the bezel having an opening, the opening aligned over the switch;
   a button in the opening, the button being sealed to the bezel and being sealed within the opening, such that the bezel, the button and the handpiece form a sealed enclosure around the switch, wherein a force applied to the button is transferred to the switch to operate the switch, the button including an arm channel that extends through a middle of the button, the arm channel intersecting perpendicularly with an insert channel;
   a button insert having a hollow cylindrical shape located at least partially within the button and within the insert channel of the button, the button insert applying outward pressure to maintain the button in the opening;
   a tube located within the button insert and in contact with the button insert, the tube applying pressure on the button insert and against the button; and
   a linkage or knob that is partially contained within the button and extends through the arm channel.

2. The handpiece of claim 1, wherein the linkage transfers to the switch the force applied to the button.

3. The handpiece of claim 2, wherein the linkage is a single straight member.

4. The handpiece of claim 1, wherein the force applied to the button is transferred to the switch by the button.

5. The handpiece of claim 1, wherein the button extends out of the opening away from the switch.

6. The handpiece of claim 1, wherein the opening extends through the bezel.

7. The handpiece of claim 1, wherein the opening extends partially through the bezel.

8. The handpiece of claim 1, wherein the bezel is sealed to the surgical handpiece using a sealing ring.

9. The handpiece of claim 1, wherein the button is sealed in the opening using a sealing ring.

10. The handpiece of claim 1, wherein the button is formed of an elastomeric material.

11. The handpiece of claim 10, wherein a bulge in the elastomeric material of the button seals the button in the opening.

12. The handpiece of claim 1, wherein the switch is one of a snap-dome switch, a tactile switch, or a conductive pill switch.

13. The handpiece of claim 1, further comprising:
   a second switch for controlling the handpiece, the second switch aligned beneath a second opening in the bezel; and
   a second button in the second opening.

14. The handpiece of claim 13, wherein, the button, the second button, the bezel, and the handpiece form a sealed enclosure around the switch and the second switch.

15. A surgical handpiece comprising:
   a switch connected to the handpiece and used for controlling the handpiece;
   a bezel with an opening, the bezel sealed to the handpiece and aligned so that the opening is over the switch;
   a flexible button in the opening, the button being sealed to the bezel and in the opening so that the button, the bezel, and the handpiece form a sealed enclosure around the switch, the flexible button including an arm channel that extends through a middle of the flexible button, the arm channel intersecting perpendicularly with an insert channel;
a linkage that transfers to the switch a force applied to the button to actuate the switch, the linkage extending through the arm channel of the flexible button; and
a button insert having a hollow cylindrical shape located at least partially within the button and within the insert channel of the flexible button, the button insert applying outward pressure to maintain the button in the opening; and
a tube located within the button insert and in contact with the button insert, the tube applying pressure on the button insert and against the button.

16. The handpiece of claim 15, wherein the linkage is a single straight member.

17. The handpiece of claim 15, wherein the opening extends partially through the bezel.

18. The handpiece of claim 15, wherein the button is formed of an elastomeric material.

19. The handpiece of claim 18, wherein a bulge in the elastomeric material of the button seals the button in the opening.

20. The handpiece of claim 15, wherein the switch wherein the switch is one of a snap-dome switch, a tactile switch, or a conductive pill switch.

21. The handpiece of claim 15, further comprising:
a second switch for controlling the handpiece, the second switch aligned beneath a second opening in the bezel; and
a second button in the second opening.

22. The handpiece of claim 21, wherein, the button, the second button, the bezel, and the handpiece form a sealed enclosure around the switch and the second switch.

* * * * *